(12) United States Patent
Kim et al.

(10) Patent No.: US 10,231,879 B2
(45) Date of Patent: Mar. 19, 2019

(54) MANUFACTURING METHOD OF MICROSTRUCTURE (71) Applicant: RAPHAS Co., Ltd., Seoul (KR)

(72) Inventors: Hong Kee Kim, Gunpo-si (KR); Jung Dong Kim, Seoul (KR); Jung Hyun Bae, Seoul (KR); Yang Gi Lee, Seoul (KR); So Hyun Park, Incheon (KR); Do Hyeon Jeong, Seoul (KR)

(73) Assignee: RAPHAS CO., LTD., Seoul (KR)

( * ) Notice: Subject to any disclaimer, the term of this patent is extended or adjusted under 35 U.S.C. 154(b) by 0 days.

(21) Appl. No.: 15/248,339

(22) Filed: Aug. 26, 2016

(65) Prior Publication Data

US 2017/0156935 A1 Jun. 8, 2017

(30) Foreign Application Priority Data

Dec. 8, 2015 (KR) ........................ 10-2015-0174066

(51) Int. Cl.
*A61F 13/02* (2006.01)
*A61K 9/00* (2006.01)
(Continued)

(52) U.S. Cl.
CPC ........ *A61F 13/0276* (2013.01); *A61K 9/0021* (2013.01); *B32B 37/12* (2013.01);
(Continued)

(58) Field of Classification Search
CPC ......... A61F 13/0276; A61F 2013/0296; A61K 9/0021; B32B 38/10; B32B 37/12; B32B 2535/00
See application file for complete search history.

(56) References Cited

U.S. PATENT DOCUMENTS 6,092,981 A * 7/2000 Pfeiffer ............. H01L 21/67303
206/710
6,099,241 A * 8/2000 Inoue ................ H01L 21/67775
414/391
(Continued)

FOREIGN PATENT DOCUMENTS

JP    2005154321 A    6/2005
KR    20100130169 A   12/2010
(Continued)

OTHER PUBLICATIONS

KR 101285085 Machine Translation of Description (EPO/Google).*

*Primary Examiner* — Michael N Orlando
*Assistant Examiner* — Cynthia L Schaller
(74) *Attorney, Agent, or Firm* — Dinsmore & Shohl LLP; Yongsok Choi, Esq.

(57) ABSTRACT

A manufacturing method of a microstructure includes providing a patch manufacturing sheet formed in a state in which a bottom layer is exposed on an upper part thereof; providing the patch manufacturing sheet on a first process substrate and a second process substrate; spotting a viscous composition at a plurality of positions spaced apart from each other on the bottom layer of the patch manufacturing sheet provided on only the first process substrate, or provided on both of the first process substrate and the second process substrate; contacting the patch manufacturing sheet provided on the second process substrate or the viscous composition to the viscous composition spotted on the patch manufacturing sheet provided on the first process substrate; moving relatively the second process substrate with respect to the first process substrate to stretch the viscous composition and to coagulate the stretched viscous composition; and cutting the coagulated viscous composition.

7 Claims, 6 Drawing Sheets

(51) Int. Cl.
*B32B 37/12* (2006.01)
*B32B 38/10* (2006.01)

(52) U.S. Cl.
CPC ...... *B32B 38/10* (2013.01); *A61F 2013/0296* (2013.01); *B32B 2535/00* (2013.01)

(56) References Cited

U.S. PATENT DOCUMENTS

| | | | |
|---|---|---|---|
| 2002/0138049 A1 | 9/2002 | Allen et al. | |
| 2007/0125483 A1* | 6/2007 | Barnett | A61K 9/703 156/152 |
| 2008/0157421 A1* | 7/2008 | Mukai | A61H 39/086 264/164 |
| 2011/0240201 A1* | 10/2011 | Jung | A61M 37/0015 156/60 |
| 2012/0251789 A1* | 10/2012 | Tanaka | H01L 21/67092 428/170 |
| 2015/0086316 A1* | 3/2015 | Greenberg | H01L 21/6838 414/752.1 |
| 2016/0053137 A1* | 2/2016 | Hayashishita | C09J 7/02 438/464 |

FOREIGN PATENT DOCUMENTS

| | | | | |
|---|---|---|---|---|
| KR | 20120068516 A | | 6/2012 | |
| KR | 101285085 | * | 7/2013 | ........ A61M 37/0015 |

* cited by examiner

MANUFACTURING METHOD OF MICROSTRUCTURE

CROSS-REFERENCE TO RELATED APPLICATIONS

This application claim priority to Korean Patent Application No. 10-2015-0174066 filed on Dec. 8, 2015, the entire contents of which are hereby incorporated by reference.

BACKGROUND

1. Technical Field

The present disclosure relates to a manufacturing method of a microstructure such as a microneedle using an air blowing method. More particularly, the present disclosure relates to a manufacturing method of a microstructure such as a microneedle using a blowing method, which improves a process of forming a bottom layer that is a basis of a microstructure formation in a conventional manufacturing method of a microstructure.

2. Description of the Related Art

Despite the development of numerous drugs, bioactive substances and the like for treating diseases, problems involving the passage of biological barriers (e.g., skin, oral mucosa, and brain-blood vessel barrier) and the efficiency of drug delivery still remain to be improved in view of delivering the drugs into a human body.

Generally, drugs and bioactive substances are orally administered in a dosage form of a tablet or capsule, but numerous drugs cannot be effectively delivered through only the above administration manner because they are digested or absorbed in the gastrointestinal tract or lost due to hepatic mechanisms. Moreover, some drugs cannot be efficiently diffused when passing through the intestinal mucosa. Also, patient compliance is problematic (for example, critical patients who need to take drugs at predetermined intervals or cannot take drugs).

Another general technique for drug delivery is to use conventional needles. While this technique is more effective than oral administration, it causes pain at the injection sites, local damage to skin, bleeding, or infections at the injection sites.

For addressing the above described problems of oral administration and a subcutaneous injection, a transdermal administration method through patches is used. While the transdermal administration using patches has advantages in that side effects are small, patient compliance is high, and maintaining blood concentration of drugs constantly is easy, this has disadvantages in that drugs permeable to skin are limited and the efficiency of drug delivery is low.

To address the above described problems, a variety of microstructures including a microneedle have been developed. Recently developed microneedles have been mainly used for in vivo delivery of drugs, blood collecting, detection of in vivo analytes, and the like.

Unlike the existing needles, the microneedle has features of painless skin penetration and causing no wounds, and a diameter of a top portion for the minimum sharpness is important in the painless skin penetration. In addition, the microneedle is required to have a sufficient physical hardness because it needs to pass through the stratum corneum of 10 to 20 µm, which is the thickest barrier in the skin. The microneedle needs to also have an appropriate length in order to improve the efficiency of drug delivery by reaching capillary vessels. Conventionally, since the proposal of an in-plane type microneedle ("Silicon-processed Microneedles," *Journal of Microelectrochemical Systems* 8, 1999), various types of microneedles have been developed. According to a method of manufacturing an out-of-plane type solid microneedle using an etching technique (disclosed in U.S. Patent Publication No. 2002138049, entitled of "Microneedle Devices and Methods of Manufacture and Use Thereof"), a solid silicon microneedle is manufactured to have a diameter of 50 to 100 µm and a length of 500 µm. However, the microneedle could not realize the painless skin penetration, and had difficulty in delivery of drugs and cosmetic ingredients to a target region.

Meanwhile, Prausnitz (Georgia Institute of Technology, U.S.A.) has suggested a method of manufacturing a biodegradable polymer microneedle by producing a mold by performing etching or photolithography on glass (Biodegradable Polymer Microneedles: Fabrication, Mechanics and Transdermal Medicine Delivery, *Journal of Controlled Release* 104, 2005, 5166). Also, in 2006, a method of manufacturing a biodegradable solid microneedle by loading a material manufactured in a capsule type onto an end part of a mold manufactured by photolithography was suggested (Polymer Microneedles for Controlled-Release Medicine Delivery, *Pharmaceutical Research* 23, 2006, 1008). According to the above described method, it is easy to load a drug which can be manufactured in a capsule type, but when a large amount of such a drug is loaded, the microneedle is degraded in hardness, and thus there is a limitation to application to a drug that needs to be administered in a large dose.

In 2005, an absorbable microneedle was manufactured by Nano Device and Systems Inc. (Japanese Patent Publication No. 2005154321; and "Sugar Micro Needles as Transdermic Drug Delivery System," *Biomedical Microdevices* 7, 2005, 185). Such an absorbable microneedle is used in drug delivery or cosmetics without removing the microneedle inserted intradermally. According to the above described method, a composition prepared by mixing maltose with a drug is applied to a mold and then solidified to thereby manufacture a microneedle. The Japanese patent discloses a manufacturing of an absorbable microneedle for transdermal absorption of drugs, but skin penetration of the absorbable microneedle is accompanied by pain.

In addition, due to a technical limitation to the manufacture of a mold, it is very difficult to manufacture a microneedle having a top portion of a suitable diameter causing no pain and a length required for effective drug delivery, that is, a length equal to or greater than 1 mm.

A biodegradable microneedle suggested by Prausnitz (Georgia Institute of Technology, U.S.A.) in 2008 was manufactured using a polydimethylsiloxane (PDMS) mold and a material prepared by mixing polyvinylpyrrolidone (PVP) with methacrylic acid (MAA) (Minimally Invasive Protein Delivery with Rapidly Dissolving Polymer Microneedles, *Advanced Materials* 2008, 1). Also, a microneedle was manufactured by injecting carboxymethylcellulose into a pyramid-structure mold (Dissolving Microneedles for Transdermal Medicine Delivery, *Biomaterials* 2007, 1). However, the method using a mold has a limitation in that a new mold and frame should be manufactured through a complicated process so as to adjust a diameter and a length of the microneedle, and further has a disadvantage in that a process of injecting a material into a mold to manufacture the micro needle is a complicated and time consuming process.

In 2008, an apparatus and a method for manufacturing a skin needle using a pin structure were presented through U.S. Patent registered by Mukai et al. of Japan (U.S. Pat. No.

20080157421A1). This method employs a technique of pulling a viscous material using a tensile force thereof with a pin by heating the viscous material at a base of a substrate. Owing to the technique of pulling a material, which is melted by heat or has viscosity, with a pin structure, a limitation of this method still remained in an increase of a manufacture cost due to a process for newly manufacturing a pin structure depending on a desired pattern, and difficulty in loading various thermosensitive biopharmaceuticals (a hormone, a vaccine, other protein drug, and the like) due to the heating process.

Meanwhile, the skin is composed of a stratum corneum (<20 μm), an epidermis (<100 μm), and a dermis (300 to 2,500 μm), which are sequentially stacked from an outer layer of the skin. Therefore, in order to deliver drugs and bioactive substances to a specific skin layer with no pain, a microneedle will be manufactured to have a diameter equal to or greater than approximately 30 μm at a top portion, an effective length of 200 to 2,000 μm, and a sufficient hardness to skin penetration such that the drugs and skin care ingredients may be effectively delivered. In addition, in order to deliver drugs, bioactive substances and the like through a biodegradable solid microneedle, it could exclude a process, which may destroy activities of the drugs and the bioactive substances, including a high heat treatment, an organic solvent treatment and the like from the microneedle manufacturing process.

A conventional solid microneedle is limited to be manufactured with a material including a silicon, polymers, a metal, a glass and the like due to a limitation of the manufacturing method, and it has disadvantages in that drug degeneration, insufficient hardness, a loss of a drug, and the like occur according to a complicated and highly time consuming manufacturing process due to a manufacturing method using a molding technique. Consequently, there are ongoing demands for a method of manufacturing a microneedle, wherein the method is capable of implementing a sufficient hardness with no specific limitation to a material while having a thin diameter to realize skin penetration with no pain and a sufficient length to deeply penetrate into a skin, and minimizing a loss of a drug.

Figure 1:
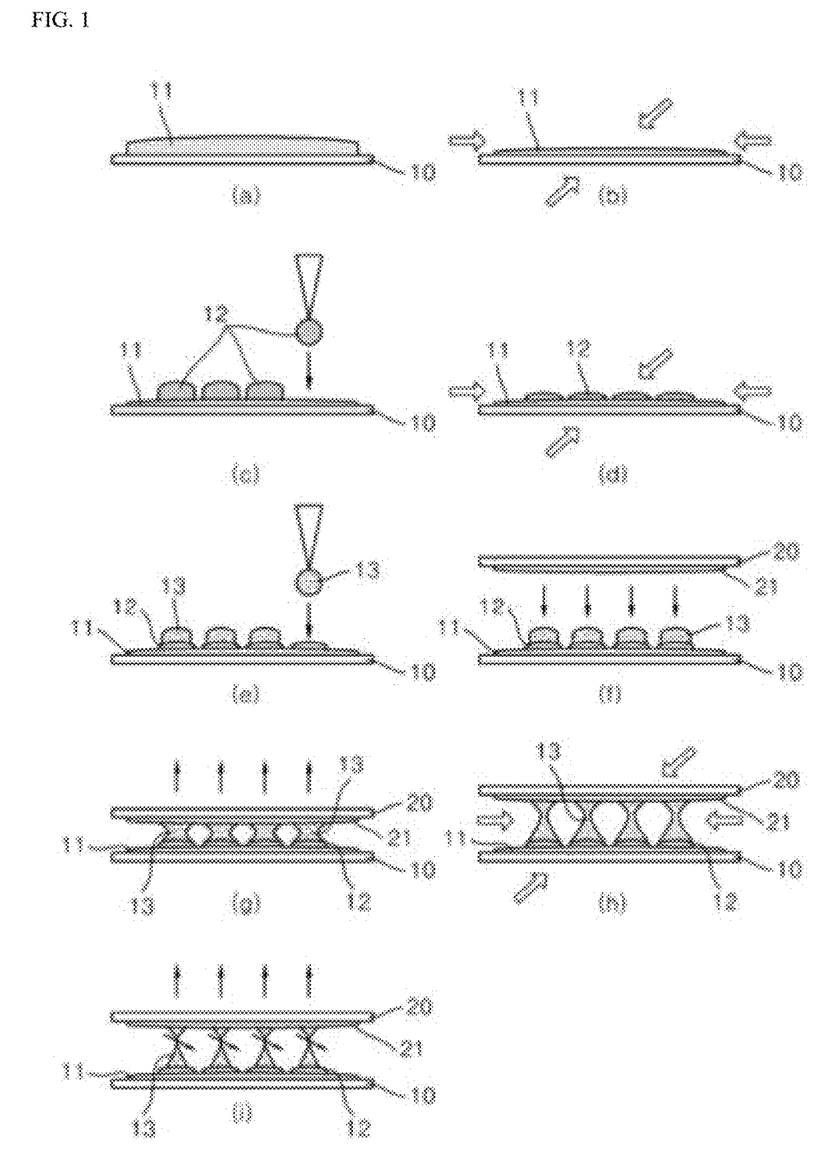
FIG. 1 is a diagram illustrating a microstructure manufacturing process of the related art, which developed by the present inventor.

To address the problems as described above, the present inventor disclosed a totally new method for manufacturing a microstructure in Korean Patent Application No. 10-2010-0130169 (Title of Invention: Method for Manufacturing a Microstructure). The method for manufacturing a microstructure is schematically shown in FIG. 1. This will be described in brief as follows.

Firstly, in a forming of a bottom layer, a first viscous material 11 is applied to a first substrate 10 and then is dried (coagulated) to form a bottom layer. At this point, an air blowing may be performed so as to facilitate the coagulation. Here, the first substrate 10 is formed in a plane shape, and any material may be applicable to the first substrate 10. For example, the first substrate 10 may be manufactured with a material including a polymer, an organic chemical material, a metal, a ceramic, a semiconductor and the like. However, when a microneedle is manufactured for medical and pharmaceutical purposes, it may be preferable to manufacture the first substrate 10 with a material that is not harmful to a human body. After Operations (Operations (a) and (b) of FIG. 1) of applying the first viscous material 11 to the first substrate 10 and coagulating it to form the bottom layer, a second viscous material 12 is spotted to form a base structure layer. As similar to the forming of the bottom layer, an air blowing may be performed to coagulate and form the base structure layer. The base structure layer is a layer that is formed by being spotted on the bottom layer for the purpose of precisely adjusting an amount of a pharmaceutical ingredient, which is injected into a human body, when another viscous material being spotted on the base structure layer, that is, a third viscous material 13 is a functional material such as a medicine and the like, and such a base structure layer may be omitted depending on a circumstance (Operations (c) and (d) of FIG. 1). After the forming of the base structure layer, the third viscous material 13, which is a material of a microneedle penetrating into the human body, is spotted on the base structure layer (Operation (e) of FIG. 1). When the base structure layer is omitted, the third viscous material 13 may be spotted on the bottom layer.

Under such a circumstance, as shown in Operation (f) of FIG. 1, a second substrate 20, on which a bottom layer is formed by the same manner as described above, is downwardly moved in a state of directing the bottom layer to face the third viscous material 13 to come into contact therewith, and thereafter, as shown in Operations (g) and (h) of FIG. 1, it is upwardly moved to stretch the third viscous material 13. The stretched third viscous material 13 is coagulated in an air blowing manner and the like. Afterward, as shown in Operation (i) of FIG. 1, the stretched third viscous material 13 is cut in a state in which the third viscous material 13 was completely coagulated so that a microneedle structure is generated.

According to the conventional microstructure manufacturing method by the present inventor as described above, it can not only realize a sufficient hardness, but reduce a loss of a functional material so that most of the above described problems may be solved.

However, in the conventional microstructure manufacturing method by the present inventor as described above, the damage to the bottom layer or the microneedle structure occurs in the course of separating the bottom layer from the first and second substrates 10 and 20 so as to attach the microneedle structure, which is formed on the bottom layer, to a patch type product that is able to adhere to the skin.

Also, there is a disadvantage in which a thickness of the bottom layer is not maintained uniformly. When a thickness of the bottom layer is thicker than an intended thickness and a stretching of the same length as described above is performed, upper and lower lengths of the microneedle, which is made of the third viscous material 13 that is spotted on the bottom layer and is stretched to be formed, may be shorter than intended upper and lower lengths, and in this case an upper end part of the microneedle does not arrive at the stratum corneum so that the efficiency of drug delivery may be reduced. In addition, at the same time, a cross-sectional diameter of the upper end part of the microneedle may be increased (a phenomenon occurs due to shortened lengths, which were stretched upwardly and downwardly, despite of spotting the same volume of a viscous material), and thus pain may be induced when the microneedle is adhered to the skin. Contrarily, when the thickness of the bottom layer is thinner than the intended thickness and a stretching of the same length as described above is performed, the cross-sectional diameter of the microneedle may be smaller than an intended cross-sectional diameter. Therefore, the upper and lower lengths may be longer than the intended upper and lower lengths to cause a decrease of the physical hardness so that a diameter and hardness, which are suitable for the skin penetration, may not be provided and thus the efficiency of drug delivery may be reduced.

Further, the thickness of the bottom layer should be uniformly maintained. When the thickness of the bottom layer is not formed uniformly, the cross-sectional diameter of the microneedle and the upper and lower lengths thereof may be varied depending on a position of the microneedle so that the physical hardness and the upper and lower lengths are not uniform as described above, and as a result, the pain may be induced or the efficiency of drug delivery may be reduced when a user adheres the microneedle to the skin.

However, according to the microstructure manufacturing method by the present inventor as described above, the bottom layer is formed after the first viscous material 11 is applied on the first substrate 10 and then is coagulated, and shortly afterward, the second and third viscous materials 12 and 13 are spotted on the bottom layer so that a next process is immediately performed without inspecting whether or not a thickness of the bottom layer is formed with an intended thickness. Consequently, there is a problem in that a defective determination can be carried out unnecessarily after the forming of the microneedle structure on the bottom layer because the defective determination cannot be carried out immediately when a thickness of the bottom layer deviates from the intended thickness.

Another additional problem is that a process time is longer. This problem also relates to a forming of the bottom layer. Because one hour at minimum to more than several hours may be typically required to dry the viscous material to form a layer, there is a problem in that productivity is decreased due to a process of applying the first viscous material 11 so as to form the bottom layer, and a consecutive coagulating process by an air blowing.

SUMMARY

An object of the present disclosure is directed to address the above described problems of the related art.

More particularly, an object of the present disclosure is directed to provide a manufacturing method of a microstructure no need for separately performing a process of attaching a bottom layer to a patch supporting layer on which an adhesive is applied after the bottom layer is separated from a substrate.

Also, an object of the present disclosure is directed to provide a manufacturing method of a microstructure, which is capable of uniformly forming a thickness of a bottom layer that is a basis at which a microneedle is formed, and inspecting uniformity of the thickness before a process is proceeded.

In addition, an object of the present disclosure is directed to provide a manufacturing method of a microstructure, which is capable of dramatically reducing a process time required to manufacture a bottom layer that is a basis at which a microneedle is formed.

A representative configuration of the present disclosure for attaining the objects is as follows.

A manufacturing method of a microstructure according to one embodiment of the present disclosure includes providing a patch manufacturing sheet 30 formed in a state in which a bottom layer 34 is exposed on an upper part thereof; providing the patch manufacturing sheet 30 on a first process substrate 50 and a second process substrate 60; spotting a viscous composition at a plurality of positions spaced apart from each other on the bottom layer 34 of the patch manufacturing sheet 30 provided on only the first process substrate 50, or provided on both of the first process substrate 50 and the second process substrate 60; contacting the patch manufacturing sheet 30 provided on the second process substrate 60, or the viscous composition, which is spotted on the patch manufacturing sheet 30 provided on the second process substrate 60, to the viscous composition spotted on the patch manufacturing sheet 30 provided on the first process substrate 50; moving relatively the second process substrate 60 with respect to the first process substrate 50 to stretch the viscous composition and to coagulate the stretched viscous composition; and cutting the coagulated viscous composition.

In the manufacturing method of a microstructure according to the present disclosure, which is configured as the above described, the providing of the patch manufacturing sheet 30 formed in a state in which the bottom layer 34 is exposed on the upper part thereof includes providing the patch manufacturing sheet 30 including a supporting layer 31, an adhesive layer 32, and a peeling film 33; removing a portion of the peeling film 30 of the patch manufacturing sheet 30 to expose the adhesive layer 32; and attaching the bottom layer 34 to the exposed adhesive layer 32, wherein the bottom layer 34 is manufactured to correspond to a size and a shape of the exposed adhesive layer 32.

Meanwhile, the providing of the patch manufacturing sheet 30 on the first process substrate 50 and the second process substrate 60 may vacuum suction the patch manufacturing sheet 30, which is stored on a sheet storing substrate 40 and to which the bottom layer 34 is attached, using a robot arm to move to the first process substrate 50 and the second process substrate 60.

By looking in detail a configuration for vacuum suctioning the patch manufacturing sheet 30 in a stored state using the robot arm to move to the substrates, a hole may be formed at the patch manufacturing sheet 30 to which the bottom layer 34 is attached, and the patch manufacturing sheet 30 to which the bottom layer 34 is attached may be passed through the hole by a bar 41, which is vertically formed at the sheet storing substrate 40, thereby being stored on the sheet storing substrate 40 in a stacked manner. In such a stored state, if the bar 41 guides a vertical movement of the patch manufacturing sheet 30 to which the bottom layer 34 is attached while the robot arm vacuum suctions and vertically moves the patch manufacturing sheet 30 to which the bottom layer 34 is attached, it may be possible to safely and precisely grip and move the patch manufacturing sheet 30.

A manufacturing method of a microstructure according to another embodiment of the present disclosure includes providing one or more patch manufacturing sheets 30 formed in a state in which an adhesive 32 is exposed on an upper part thereof; providing the one or more patch manufacturing sheets 30 on a first process substrate 50 and a second process substrate 60; spotting a viscous composition at a plurality of positions spaced apart from each other on the adhesive layer 32 of the one or more patch manufacturing sheets 30 provided on the first process substrate 50 and/or the second process substrate 60; contacting the patch manufacturing sheet 30 provided on the second process substrate 60, or the viscous composition, which is spotted on the patch manufacturing sheet 30 provided on the second process substrate 60, to the viscous composition spotted on the patch manufacturing sheet 30 provided on the first process substrate 50; moving relatively the second process substrate 60 with respect to the first process substrate 50 to stretch the viscous composition and to coagulate the stretched viscous composition; and cutting the coagulated viscous composition. Here, the important thing is that an adhesive configuring the adhesive layer 32 should be a hydrophilic material.

The providing of the patch manufacturing sheet 30 formed in a state in which the adhesive layer 32 is exposed on the upper part thereof among the present embodiment includes providing the patch manufacturing sheet 30 including a supporting layer 31, the adhesive layer 32, and a peeling film 33; and removing a portion of the peeling film 30 of the patch manufacturing sheet 30 to expose the adhesive layer 32.

According to the present disclosure, the problems, which have been described in Background, of the related art are solved.

More particularly, in accordance with the present disclosure, it is provided a manufacturing method of a microstructure no need for separately performing a process of attaching a bottom layer to a patch on which an adhesive is formed to be attached to a skin after the bottom layer is separated from a substrate.

Also, in accordance with the present disclosure, it is provided a manufacturing method of a microstructure, which is capable of uniformly forming a thickness of a bottom layer that is a basis at which a microneedle is formed, and inspecting uniformity of the thickness before a process is proceeded.

Further, in accordance with the present disclosure, it is provided a manufacturing method of a microstructure, which is capable of dramatically reducing a process time required to manufacture a bottom layer that is a basis at which a microneedle is formed.

BRIEF DESCRIPTION OF DRAWINGS

The above and other objects, features and advantages of the present disclosure will become more apparent to those skilled in the art by describing in detail exemplary embodiments thereof with reference to the accompanying drawings, in which.

DETAILED DESCRIPTION

The following detailed description with respect to the present disclosure will be described with reference to the accompanying drawings illustrating as examples of specific embodiments which can implement the present disclosure. These embodiments will be fully described in detail for allowing a person skilled in the art to implement the present disclosure. It should be understood that various embodiments of the present disclosure are different from each other, but they are not to be exclusive mutually. For example, specific shapes, structures, and features disclosed herein may be implemented by another embodiment in association with one embodiment without departing from the spirit and scope of the present invention. Also, it should be understood that positions and arrangements of respective components disclosed in each embodiment may be modified without departing from the spirit and scope of the present disclosure. The detailed description to be disclosed later, therefore, is not to be taken in a sense for limiting the scope of the present disclosure but for explanation thereof, and the scope of the present disclosure should be construed by the appended claims, along with the full range of equivalents to which such claims are entitled. In giving reference numerals to components of the drawings, the same or similar reference numerals are given to components having the same or similar functions throughout various aspects.

Hereinafter, for easily implementing the present disclosure by those skilled in the art, various preferable embodiments of the present disclosure will be described in detail with reference to the accompanying drawings.

Figure 2:
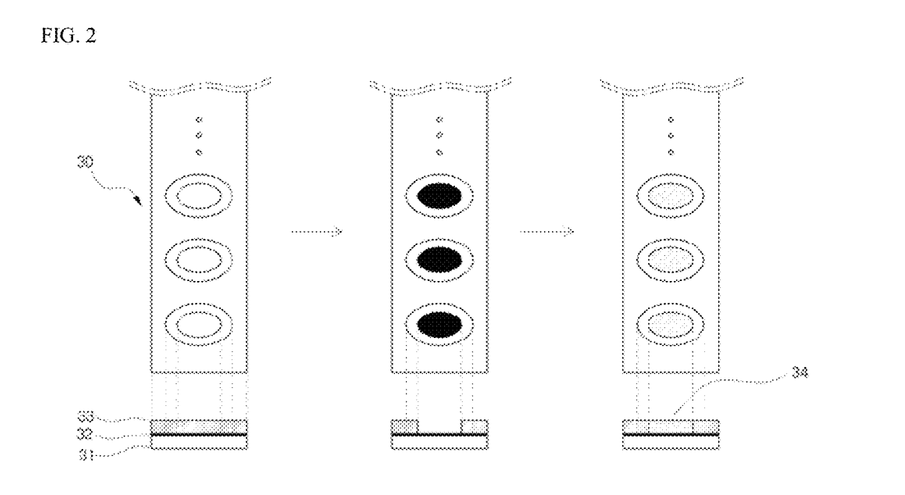
FIG. 2 is a diagram illustrating a manufacturing process of a patch manufacturing sheet according to one embodiment of the present disclosure.

FIG. 2 illustrates a manufacturing process of a patch manufacturing sheet 30 that is used in a method according to the present disclosure.

A top view and a cross-sectional view of the patch manufacturing sheet 30 are shown in FIG. 2. A supporting layer 31 is provided as a component of the patch manufacturing sheet 30. The supporting layer 31 may be made of a material having superior moisture permeability and stretchability and blocking penetration of drugs and bioactive substances, and a film may be used, wherein the film may be configured with one or more materials selected, for example, among a paper, a non-woven fabric, a woven fabric, a natural or synthetic rubber, polyethylenes terephthalate, polyvinyl chloride, polypropylene, polyurethane, polystyrene, polycarbonate, polyethylenes terephthalate glycol, poly(ethylene-co-vinyl alcohol), polyethylene, polyester, and nylon.

An adhesive layer 32 is located on an upper surface of the supporting layer 31. An adhesive used in the adhesive layer 32 is configured with a pressure sensitive adhesive component that is pharmaceutically usable, and a hydrophilic or organic solvent material and the like may be used. As such an adhesive polymer material, an acrylate based resin including an acrylate polymer, a vinyl acetate-acrylate copolymer and the like, a copolymer resin including a polyisobutylene, polystyrene, or polybutadiene copolymer, a rosin based resin, a polyterpene resin, a petroleum based resin, a terpene phenol resin, a silicon polymer, and a natural or synthetic rubber, or a mixture thereof may be used. A single adhesive polymer material or two or more mixed adhesive polymer material may be used.

A peeling film 33 is formed on an upper surface of the adhesive layer 32. As shown in FIG. 2, if the peeling film 33 is attached to the adhesive layer 32 while a cutting plane line of an approximate double oval shape (not limited to this shape) is formed at the peeling film 33, a portion thereof at which the cutting plane line is formed to be separable from another portion of the peeling film 33, for example, a central small oval portion of the double oval may be easily separated.

If the providing of the patch manufacturing sheet 30 of the structure described above is a first procedure of the manufacturing process, the removing of the central oval portion of the peeling film 33 using the pre-formed cutting plane line thereof is a second procedure, and this second procedure corresponds to a second diagram from a left side of FIG. 2. When the central oval portion of the peeling film 33 is removed, a portion of the adhesive layer 32 corresponding to the removed central oval portion is exposed.

Next, a bottom layer 34 is covered on the exposed adhesive layer 32. The term of the bottom layer 34 is used as a meaning of a bottom at which a microstructure is formed. The bottom layer 34 is come into contact with an adhesive of the adhesive layer 32 to maintain a firm coupled state. The bottom layer 34 may be any film having a hydrophilic surface so as to allow a microstructure to be formed thereon. Preferably, the bottom layer 34 may be any film having a constant and uniform thickness and a hydrophilic group on a surface thereof. More preferably, the bottom layer 34 may be a hydrophilic polymer film having stretchability of a proper level so as to be tightly attached to a curved portion.

One of features of the present disclosure is that the bottom layer 34 may be manufactured in advance in a separate process from a microstructure forming process to be attached to the patch manufacturing sheet 30, without being manufactured by the applying procedure of a hydrophilic viscous material and the drying procedure in the microstructure forming process as described in the related art.

Figure 3:
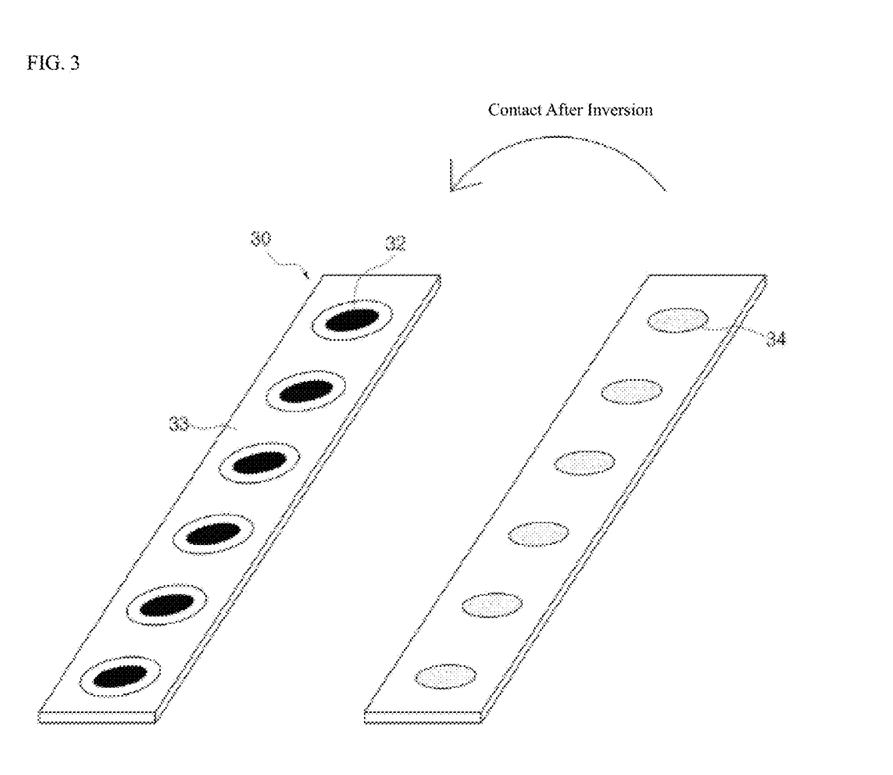
FIG. 3 is a diagram for describing a method for integrally attaching a bottom layer to an exposed adhesive layer of the patch manufacturing sheet among the manufacturing process of a patch manufacturing sheet according to one embodiment of the present disclosure.

According to the method of the present disclosure, the bottom layer 34 may be coupled to each of a plurality of exposed adhesive layers 32 which are formed at the patch manufacturing sheet 30, whereas, in order to reduce a time required for a process and to increase accuracy of a coupling, the bottom layer 32 and the exposed adhesive layer 32 may be coupled to each other with a method shown in FIG. 3.

In FIG. 3, bottom layers 34 are formed on a sheet that is manufactured in a size the same as that of the patch manufacturing sheet 30. A shape and a size of each of the bottom layers 34 correspond to those of each of exposed adhesive layers 32, and a position of each of the bottom layers 34 on the sheet corresponds to that of each of the exposed adhesive layers 32. After the sheet at which the bottom layers 34 have been formed in the above described state is prepared, the sheet is inverted to be come into contact with the patch manufacturing sheet 30 having the exposed adhesive layers 32 while the bottom layers 34 face a lower direction. When the sheet at which the bottom layers 34 have been formed is come into contact with the patch manufacturing sheet 30 under a condition in that the shape, size, position of each of the bottom layers 34 are exactly corresponded as described above, each of the bottom layers 34 is coupled to a corresponding one of the exposed adhesive layers 32 and thus such a coupled state is firmly maintained by a coupling force of the adhesive layer 32. Thereafter, when the sheet at which the bottom layers 34 are formed is released from the contact with the patch manufacturing sheet 30, the plurality of bottom layers 34 may be exactly coupled to all the exposed adhesive layers 32 formed at the patch manufacturing sheet 30 at the same time.

In addition to the above described method, after the sheet at which the plurality of bottom layers 34 have been formed is inverted to be come into contact with the patch manufacturing sheet 30 having the exposed adhesive layers 32, an inverted sheet surface (a surface of the sheet opposite to a surface thereof at which the plurality of bottom layers 34 have been formed) of the sheet is pressurized by means of a pressurizing device so that a contact state between the bottom layer 34 and the exposed adhesive layer 32 may be certainly accomplished. The pressurizing device may be, for example, a roller type or a flat type. When such a pressurizing method is employed, a forming of a strong contact state may be secured and also a constant pressure is pressurized to an entire of the bottom layer 34 of which is important to be formed with a uniform thickness so that a function of eliminating a certain amount of non-uniformity, which might exist in a thickness of the bottom layer 34 coupled to the patch manufacturing sheet 30, may be performed before the bottom layer 34 is input to the microstructure manufacturing process.

Before being provided to the manufacturing process of the patch manufacturing sheet 30 according to the present disclosure as described above, the bottom layer 34 may be undergone a quality control (QC) process that inspects whether or not the thickness and the like of the bottom layer 34 are manufactured to satisfy a predetermined criterion. Consequently, it may be possible to previously prevent a defect of the microstructure, which may occur when the thickness of the bottom layer 34 being a basis of the formation of the microstructure does not satisfies the predetermined criterion.

Figure 4:
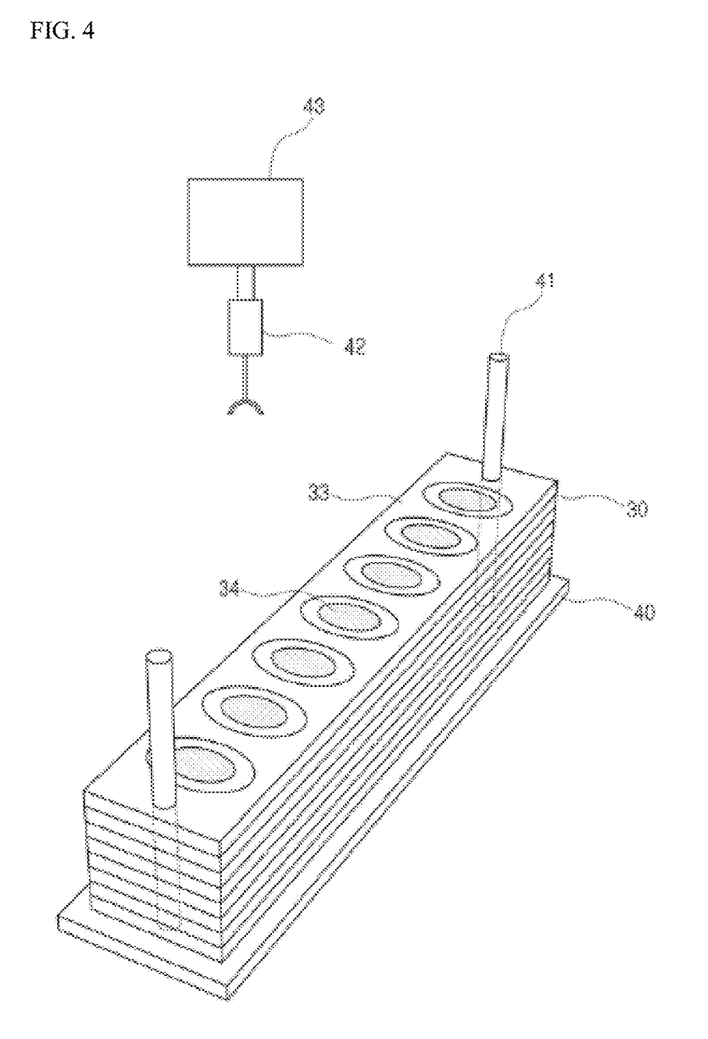
FIG. 4 is a diagram for describing a method in which the patch manufacturing sheet manufactured according to one embodiment of the present disclosure is stored before being input to a microstructure manufacturing process and is input thereto.

A plurality of patch manufacturing sheets 30, each of which is formed to be coupled to the bottom layer 34, may be manufactured and then they are provided by one at a time or at the same time to the microstructure forming process. For example, they may be provided to the microstructure forming process under a state as shown in FIG. 4. With reference to FIG. 4, a hole may be provided at upper and lower parts of the patch manufacturing sheet 30 at which a plurality of patches are formed, and the patch manufacturing sheet 30 may be exactly position-aligned by a bar 41 passing through the hole and may be stacked in plural numbers on a sheet storing substrate 40 to be provided to the microstructure forming process.

When the plurality of patch manufacturing sheets 30 being stacked as in the state described above are provided to the microstructure forming process, as a first procedure of the microstructure forming process, for example, a robot arm including a vacuum suction unit 42 downwardly moves to vacuum suction an upper surface of each of the stored patch manufacturing sheets 30 and then it moves upwardly so that the individual patch manufacturing sheet 30 is guided and upwardly moved along the bars 41 through the holes formed at upper and lower parts of the individual patch manufacturing sheet 30, thereby escaping from the stored state. Because an actuator 43 performing upward, downward, left, and right movements is controlled by a controller, the robot arm may be able to exactly deliver the patch manufacturing sheet 30 to a predetermined substrate position in the microstructure forming process. Meanwhile, in addition that the plurality of patch manufacturing sheets 30 are stacked to be provided to the process as described above, it should be understood that various type process provision methods may be applicable. For example, a single patch manufacturing sheet 30 may be provided to the process in a state of being stored on the sheet storing substrate 40.

Figure 5:
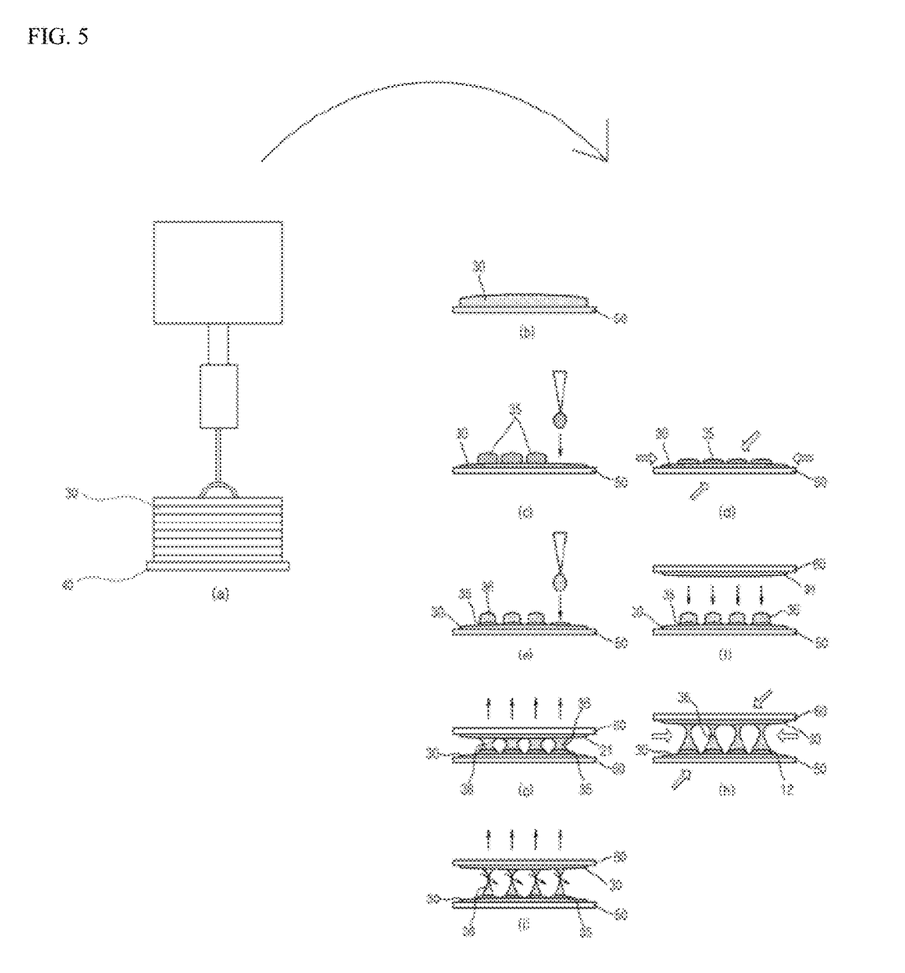
FIG. 5 is a diagram illustrating a process in which a microstructure is formed on the patch manufacturing sheet according to one embodiment of the present disclosure.

A microstructure forming process on the patch manufacturing sheet 30 according to the present disclosure is shown in FIG. 5.

First, a robot arm approaches and grips the patch manufacturing sheet 30, which is stored on the sheet storing substrate 40 and to which the bottom layer 34 was coupled, using a vacuum suction unit (Operation (a)).

And then, the robot arm moves to a position at which the microstructure forming process is performing, and downwardly moves to seat the patch manufacturing sheet 30, to which the bottom layer 34 was coupled, on a first process substrate 50 (Operation (b)).

Thereafter, a forming of a base structure layer is performed. The base structure layer is formed by spotting a viscous material on the patch manufacturing sheet 30 to which the bottom layer 34 was coupled. When a microstructure to be used for medical and pharmaceutical purposes is manufactured such as the microneedle according to the present embodiment, a viscous material may be preferable to include a "biocompatible or biodegradable material." Here, the "biocompatible material" means a material having no toxicity to a human body and a chemical inert property. And, the "biodegradable material" means a material that can be decomposed within a human body by body fluid, enzyme, microorganism, or the like.

Also, in accordance with the present embodiment, the viscous material may be preferable to be dissolved in a proper solvent to appear viscosity. In other words, among materials appearing viscosity, viscosity may appear in a state of being melted by heat, but it may appear by dissolving in a solvent.

The viscous material may include hyaluronic acid or its salt, polyvinylpyrrolidone, polyvinyl alcohol, cellulose polymer, dextran, gelatin, glycerine, polyethylene glycol, polysorbate, propylene glycol, povidone, carbomer, gum ghatti, guar gum, glucomannan, glucosamine, dammar gum, rennet casein, locust bean gum, microfibrillated cellulose, psyllium seed gum, xanthan gum, arabino galactan, arabic gum, alginic acid, gelatin, gellan gum, carrageenan, karaya gum, curdlan, chitosan, chitin, tara gum, tamarind gum, tragacanth gum, furcelleran, pectin, pullulan and the like.

More preferably, the viscous material used in the present disclosure may be hydroxypropyl methylcellulose, hydroxyalkyl cellulose, ethyl hydroxyethylcellulose, alkyl cellulose, and carboxymethyl cellulose. Most preferably, the viscous material used in the present disclosure may be carboxymethyl cellulose.

Also, the solvent for dissolving the viscous material is not specifically limited, and water, absolute or hydrous lower alcohol containing between 1 and 4 carbon atoms, acetone, ethyl acetate, chloroform, 1,3-butylene glycol, hexane, diethyl ether, or butyl acetate may be used as the solvent, and preferably, water or lower alcohol may be used as the solvent, and most preferably, water may be used as the solvent.

In the forming of a base structure layer, as shown in Operations (c) and (d) of FIG. 5, a viscous material forming a base structure layer 35 is spotted at positions spaced apart from each other on the exposed bottom layer 34 at the upper part of the patch manufacturing sheet 30 which is formed by including the bottom layer 34, and then it is coagulated to form the base structure layer 35. At this point, an air blowing may be performed so as to facilitate a coagulation of the viscous material. In Operation (d) of FIG. 5, an arrow represents that the air blowing is performed.

As an amount of the viscous material used for forming the base structure layer 35 is gradually increased, a diameter of the base structure layer 35 is increased. And, as described later, in order to spot a large amount of a viscous composition containing a functional material on the base structure layer 35, it may be preferable to largely form the diameter of the base structure layer 35. The reason is that the viscous composition overflows outside the base structure layer 35 when a large amount of the viscous composition is spotted in a state that the diameter of the base structure layer 35 is small, thereby causing a loss of the functional material that should be delivered to the human body. Meanwhile, the base structure layer 35 may be formed as high as a desired height by repeating the method for spotting and coagulating the viscous material for forming the base structure layer 35 after the base structure layer 35 has been formed through the coagulation of the viscous material.

In the embodiment of FIG. 5, the base structure layer 35 is formed and then the viscous composition is spotted thereon to form a functional material layer 36, whereas in some cases it may be possible to implement an embodiment in which a single functional material layer 36 is formed on the bottom layer 34 without forming two layers of the base structure layer 35 and the functional material layer 36 by repetitively performing the spotting.

When a drug is mixed with the viscous composition, the forming of the base structure layer 35 is omitted and a microneedle is formed with only the functional material layer 36 so that the drug is uniformly distributed to an entire of the microneedle. In this case, the drug contained in a lower end part of the microneedle may not be totally absorbed into the skin and thus may reside on the bottom layer 34 to reduce a dose amount of a drug so that it may be preferable to form the base structure layer 35 so as to maximize absorbability of a drug. On the other hand, when the drug is not mixed with the viscous composition, or a need for controlling a dose amount is relatively low, the forming of the base structure layer 35 may be omitted so as to simplify the process and increase efficiency. In Operation (e) of FIG. 5, the functional material layer 36 is formed with a viscous composition containing a functional material on the base structure layer 35. Here, the viscous composition may be made by mixing the viscous material described above with a functional material. Specifically, because the viscous composition penetrates into the skin in the case of the microneedle as in the present embodiment, it may be preferable to use a viscous material having superior biocompatible and biodegradable characteristics. Here, the functional material includes a material, which penetrates into a skin to act a specific function such as pharmaceutical efficacy, for example, a chemical drug, a protein medicine, a peptide medicine, a nucleic acid molecule for treating a gene, a nanoparticle cosmetic ingredient (for example, a wrinkle-diminishing agent, a skin aging inhibitor, and a skin whitening agent), and the like.

In Operation (f) of FIG. 5, a second process substrate 60 and the patch manufacturing sheet 30 seated thereon are used. With the similar method described above, the bottom layers 34 are formed in advance at the patch manufacturing sheet 30 seated on the second process substrate 60.

The seating of the patch manufacturing sheet 30 on the second process substrate 60 may be performed by the robot arm as similar to the seating of the patch manufacturing sheet 30 on the first process substrate 50. The robot arm may suction and support a single patch manufacturing sheet 30 stored on the sheet storing substrate 40 or a plurality of patch manufacturing sheets 30 which are stacked and stored thereon to seat on a predetermined exact position on the second process substrate 60. As shown in Operation (f) of FIG. 5, the second process substrate 60 and the patch manufacturing sheet 30 being seated thereon are inverted to be moved over the first process substrate 50 and the patch manufacturing sheet 30 being seated thereon. In order to prevent a position at which the patch manufacturing sheet 30 has been seated from being changed while such an inversion is performed, the second process substrate 60 may include a structure such as a vacuum suction structure and the like. In addition to the vacuum suction structure, it should be understood that all structures capable of maintaining the position at which the patch manufacturing sheet 30 has been seated may be included in the scope of the present disclosure.

In Operation (g) of FIG. 5, the second process substrate 60 is downwardly moved and the patch manufacturing sheet 30 seated thereon comes into contact with the functional material layer 36 spotted on the first process substrate 50. More particularly, the bottom layer 34 of the patch manufacturing sheet 30 seated on the second process substrate 60 comes into contact with the functional material layer 36 on the basis of the base structure layer 35 formed on the bottom layer 34 of the patch manufacturing sheet 30 seated on the first process substrate 50. Meanwhile, in the present disclosure, like the patch manufacturing sheet 30 seated on the first process substrate 50, a spotting of the viscous composition may be performed on the patch manufacturing sheet 30 seated on the second process substrate 60. In this case, when the second process substrate 60 is inverted and then is downwardly moved, the viscous composition, which is spotted on the patch manufacturing sheet 30 provided on the second process substrate 60, comes into contact with the viscous composition, that is, the functional material layer 36, which is spotted on the patch manufacturing sheet 30 provided on the first process substrate 50. In a stretching and a coagulating corresponding to Operations (g) and (h) of FIG. 5, the second process substrate 60 is relatively moved with respect to the first process substrate 50 (or, the first process substrate 50 is moved with respect to the second process substrate 60), and thus the functional material layer 36 is stretched and is coagulated in the stretched state. Conditions of the stretching and the coagulating are described in detail in the description of Korean Patent Application No. 10-2010-0130169 (Title of Invention: Method for Manufacturing a Microstructure) referred to as the related art of the present disclosure, and implementation of the stretching and the coagulating in corresponding Operations of the present disclosure may be performed according to the conditions described in the above-mentioned Korean Patent Application.

After the stretching and the full coagulating of the functional material layer 36 are completed, a portion having a minimum diameter of the functional material layer 36 is cut as shown in Operation (i) of FIG. 5. Such a cutting is made by additionally proceeding a relative movement between the first process substrate 50 and the second process substrate 60 under a state in which the functional material layer 36 has been coagulated. According to repetitive experiment results by the present inventor, it turned out that the portion having the minimum diameter of the functional material layer 36 can be properly cut by an additional stretching in the coagulated state. Consequently, a microneedle structure is formed at both of the patch manufacturing sheet 30 seated on the second process substrate 60 and the patch manufacturing sheet 30 seated on the first process substrate 50.

When Operations described with reference to FIG. 5 are completed and then the patch manufacturing sheet 30 is eliminated from each of the first process substrate 50 and the second process substrate 60, the patch manufacturing sheet 30 at which the microstructure (microneedle) was formed may be provided.

The patch manufacturing sheet 30, at which such a microstructure was formed, may be subject to a packaging treatment for protecting the microstructure formed on the sheet, thereby immediately being commercialized.

In the related art, in the course of separating a bottom layer from a substrate, damage to the bottom layer itself or damage to a microstructure formed on the bottom layer was frequently generated. On the other hand, according to the method of the present disclosure, the supporting layer 31, which is to form a body of a patch product when being used as the patch product in the future, is formed in plural numbers on the patch manufacturing sheet 30, the patch manufacturing sheet 30 is provided to the microstructure manufacturing process in a state in which the bottom layer 34 is coupled in advance to the supporting layer 31, and the microstructure is formed on the strong basis so that it may hardly damage the bottom layer 34 and the microstructure in the course of being separated from the substrate after the forming process of the microstructure is completed.

Next, another embodiment of the present disclosure will be described with reference to FIG. 6. Another embodiment of FIG. 6 is different from the above described embodiment in terms of an aspect in which a bottom layer 34 is not separately formed.

As described above, a bottom layer 34 is a component serving a function of a bottom at which a microstructure is formed, and it may be any film having a hydrophilic surface so as to allow the microstructure to be formed on the bottom layer 34. Also, such a bottom layer 34 is attached to an adhesive layer 32 which is exposed by removing a central portion of a peeling film 33 along a cutting plane line formed on the peeling film 33 that is a component of a patch manufacturing sheet 30 in the above described embodiment.

The present embodiment is characterized in that a viscous material configuring the adhesive layer 32 is made of a hydrophilic material that allows the microstructure to be formed thereon instead of not forming the bottom layer 34 separately.

Figure 6:
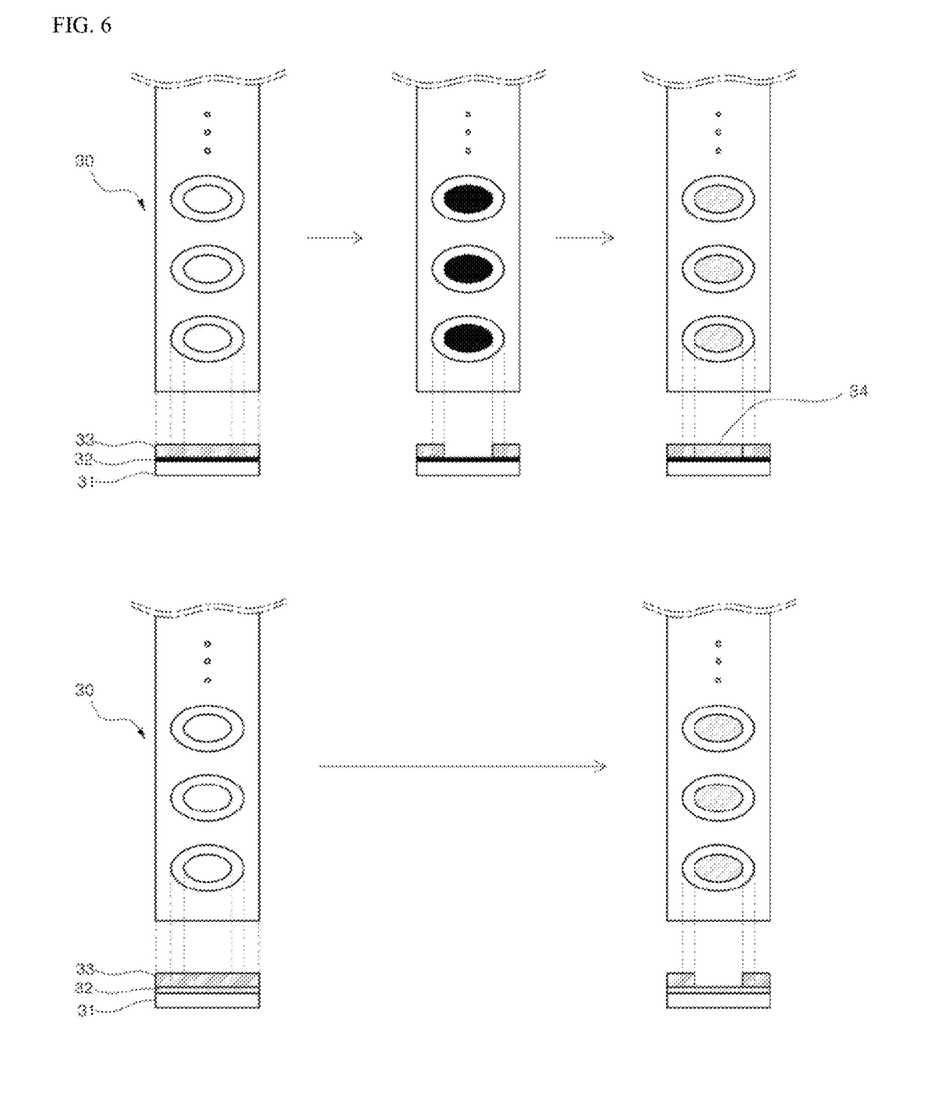
FIG. 6 is a diagram illustrating a manufacturing process of a patch manufacturing sheet according to another embodiment of the present disclosure.

By comparing with the embodiment of FIG. 2, the above described embodiment related to FIG. 2 is shown in an upper portion of FIG. 6 and the present embodiment is shown in a lower portion of FIG. 6.

In the embodiment of FIG. 2, the manufacturing process of the patch manufacturing sheet 30 is configured with the providing of a sheet in a first Operation, the removing of the central portion of the peeling film 33 in a second Operation, and the coupling of the bottom layer 34 in a third Operation, whereas in the embodiment of FIG. 6, the manufacturing process of the patch manufacturing sheet 30 is configured only with a providing of a sheet in a first Operation, and a removing of a central portion of the peeling film 33 in a second Operation.

As described above, when the viscous material configuring the adhesive layer 32 is made of the hydrophilic material that allows the microstructure to be formed thereon, there is an advantage in that the manufacturing process of the patch manufacturing sheet 30 is simplified.

The hydrophilic material configuring the adhesive layer 32, which may be usable in the present embodiment, is an adhesive polymer material having a hydrophilic group. Preferably, the hydrophilic material configuring the adhesive layer 32, which may be usable in the present embodiment, may be a hydrophilic adhesive polymer material which is medically and pharmaceutically usable and has pressure sensitivity. For example, a commercially available product containing an acrylate group resin such as an acrylate polymer, a vinyl acetate-acrylate copolymer, and the like may be used.

As described above, the patch manufacturing sheet 30 at which the bottom layer 34 is not separately formed may be implemented in a double layer of the base structure layer 35 and the functional material layer 36, and also it may be implemented to functionally omit the base structure layer 35.

What is claimed is:

1. A manufacturing method of a microstructure, comprising:

providing a patch manufacturing sheet formed in a state in which a bottom layer is exposed;

subsequently providing the patch manufacturing sheet on a first process substrate and a second process substrate;
subsequently spotting a viscous composition at a plurality of positions spaced apart from each other on the bottom layer with respect to only the patch manufacturing sheet provided on the first process substrate, or at a plurality of positions spaced apart from each other on each of the bottom layers with respect to both of the patch manufacturing sheets provided on the first process substrate and the patch manufacturing sheets provided on the second process substrate;
contacting the patch manufacturing sheet provided on the second process substrate to the viscous composition spotted on the patch manufacturing sheet provided on the first process substrate, or contacting the viscous composition, which is spotted on the patch manufacturing sheet provided on the second process substrate, to the viscous composition spotted on the patch manufacturing sheet provided on the first process substrate;
separating relatively a vertical direction distance between the first process substrate and the second process substrate to stretch the viscous composition and to coagulate the stretched viscous composition; and
cutting the coagulated viscous composition,
wherein the providing of the patch manufacturing sheet formed in a state in which the bottom layer is exposed includes:
providing the patch manufacturing sheet including a supporting layer, an adhesive layer, and a peeling film;
removing a portion of the peeling film of the patch manufacturing sheet to expose the adhesive layer; and
attaching the bottom layer to the exposed adhesive layer, wherein the bottom layer is manufactured to correspond to a size and a shape of the exposed adhesive layer.

2. The manufacturing method of claim 1, wherein the providing of the patch manufacturing sheet on the first process substrate and the second process substrate vacuum suctions the patch manufacturing sheet, which is stored on a sheet storing substrate and to which the bottom layer is attached, using a robot arm to move to the first process substrate and the second process substrate.

3. The manufacturing method of claim 2, wherein a hole is formed at the patch manufacturing sheet to which the bottom layer is attached, the patch manufacturing sheet to which the bottom layer is attached is passed through the hole by a bar, which is vertically formed at the sheet storing substrate, thereby being stored on the sheet storing substrate in a stacked manner, and the bar guides a vertical movement of the patch manufacturing sheet to which the bottom layer is attached while the robot arm vacuum suctions and vertically moves the patch manufacturing sheet to which the bottom layer is attached.

4. The manufacturing method of claim 1, wherein a top surface of the bottom layer is flush with a top surface of the peeling film after the bottom layer is attached to the exposed adhesive layer.

5. The manufacturing method of claim 1, wherein the bottom layer has a uniform thickness and maintains the uniform thickness when the bottom layer is attached to the exposed adhesive layer.

6. The manufacturing method of claim 1,
wherein removing a portion of the peeling film of the patch manufacturing sheet to expose the adhesive layer comprises:
attaching the peeling film on the adhesive layer, the peeling film including a cutting plane line corresponding to the portion of the peeling film; and
removing the portion of the peeling film from the adhesive layer.

7. A manufacturing method of a microstructure, comprising:
providing a patch manufacturing sheet formed in a state in which an adhesive layer is exposed;
subsequently providing the patch manufacturing sheet on a first process substrate and a second process substrate;
subsequently spotting a viscous composition at a plurality of positions spaced apart from each other on the adhesive layer with respect to only the patch manufacturing sheet provided on the first process substrate, or at a plurality of positions spaced apart from each other on each of the adhesive layers with respect to both of the patch manufacturing sheet provided on the first process substrate and the patch manufacturing sheet provided on the second process substrate;
contacting the patch manufacturing sheet provided on the second process substrate to the viscous composition spotted on the patch manufacturing sheet provided on the first process substrate, or contacting the viscous composition, which is spotted on the patch manufacturing sheet provided on the second process substrate, to the viscous composition spotted on the patch manufacturing sheet provided on the first process substrate;
separating relatively a vertical direction distance between the first process substrate and the second process substrate to stretch the viscous composition and to coagulate the stretched viscous composition; and
cutting the coagulated viscous composition, wherein an adhesive configuring the adhesive layer is a hydrophilic material, and
wherein the providing of the patch manufacturing sheet formed in a state in which the adhesive layer is exposed includes:
providing the patch manufacturing sheet including a supporting layer, the adhesive layer, and a peeling film; and
removing a portion of the peeling film of the patch manufacturing sheet to expose the adhesive layer.

* * * * *